United States Patent
Flynn et al.

(10) Patent No.: US 8,155,755 B2
(45) Date of Patent: Apr. 10, 2012

(54) DISPOSABLE SHEATH FOR TELEMENTRY LEADS OF A MONITORING DEVICE

(75) Inventors: Dawn Flynn, Phoenix, AZ (US); Faith OverStreet, Glendale, AZ (US); Craig Orsini, Pheonix, AZ (US)

(73) Assignee: Dignity Health, San Francisco, CA (US)

( * ) Notice: Subject to any disclaimer, the term of this patent is extended or adjusted under 35 U.S.C. 154(b) by 1245 days.

(21) Appl. No.: 11/214,090

(22) Filed: Aug. 29, 2005

(65) Prior Publication Data

US 2007/0044809 A1  Mar. 1, 2007

(51) Int. Cl.
- A61B 5/04 (2006.01)
- A61N 1/00 (2006.01)
- H02G 15/22 (2006.01)
- H01J 5/00 (2006.01)
- H01B 7/18 (2006.01)

(52) U.S. Cl. ......... 607/116; 600/392; 600/393; 174/19; 174/50; 174/103; 206/390; 248/65

(58) Field of Classification Search ......... 600/392–393; 607/116; 174/19, 50, 103; 206/390; 248/65
See application file for complete search history.

(56) References Cited

U.S. PATENT DOCUMENTS

| | | | | |
|---|---|---|---|---|
| 1,529,644 A * | 3/1925 | Atkinson et al. | ................. | 174/19 |
| 3,979,050 A * | 9/1976 | Cilia | ............................... | 383/35 |
| 4,034,853 A | 7/1977 | Smith | | |
| 4,091,922 A * | 5/1978 | Egler | ........................... | 206/364 |
| 4,349,404 A * | 9/1982 | Changani et al. | .......... | 156/308.4 |
| 4,602,638 A | 7/1986 | Adams | | |
| 4,677,697 A * | 7/1987 | Hayes | ................................ | 2/159 |
| 5,025,503 A * | 6/1991 | O'Brien | ............................ | 2/163 |
| 5,404,876 A | 4/1995 | DiSabito et al. | | |
| 5,611,338 A * | 3/1997 | Gallup et al. | .................. | 600/342 |
| 5,817,151 A * | 10/1998 | Olson et al. | .................... | 607/142 |
| 6,027,460 A * | 2/2000 | Shturman | ...................... | 600/585 |
| 6,168,019 B1 * | 1/2001 | Olson | ............................ | 206/390 |
| 6,179,786 B1 | 1/2001 | Young | | |
| 6,416,474 B1 | 7/2002 | Penner et al. | | |
| 2001/0000187 A1 | 4/2001 | Peckham et al. | | |
| 2002/0082644 A1 | 6/2002 | Picardo et al. | | |
| 2002/0107435 A1 * | 8/2002 | Swetlik et al. | ................ | 600/382 |
| 2002/0170728 A1 * | 11/2002 | Holland et al. | .................. | 174/19 |
| 2003/0236452 A1 | 12/2003 | Melker et al. | | |
| 2004/0199236 A1 * | 10/2004 | Laske et al. | .................... | 607/129 |
| 2004/0200635 A1 * | 10/2004 | Menze et al. | .................. | 174/103 |

FOREIGN PATENT DOCUMENTS

| DE | 003814215 | * 11/1989 |
|---|---|---|
| DE | 3814215 A1 | * 11/1989 |

* cited by examiner

*Primary Examiner* — Niketa Patel
*Assistant Examiner* — Nicole F Lavert
(74) *Attorney, Agent, or Firm* — Howard & Howard Attorneys PLLC

(57) ABSTRACT

A pair of sheets defining a disposable sheath for covering the electrical leads in a monitoring system used for monitoring patient vital signs and secured together along edges and along spaced seams to define a plurality of longitudinally extending compartments. A plurality of tear lines extend along the spaced seams from the second end to a distance spaced from the first end for laterally separating the compartments into separate arms, and fingers, whereby electrical leads may be bundled together in the open distance at the first end and inserted into the arms and fingers. A seal seals the sheets about the electrical leads at the respective ends.

10 Claims, 3 Drawing Sheets

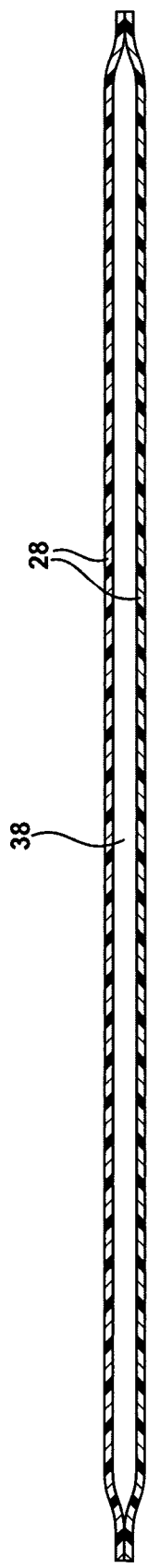
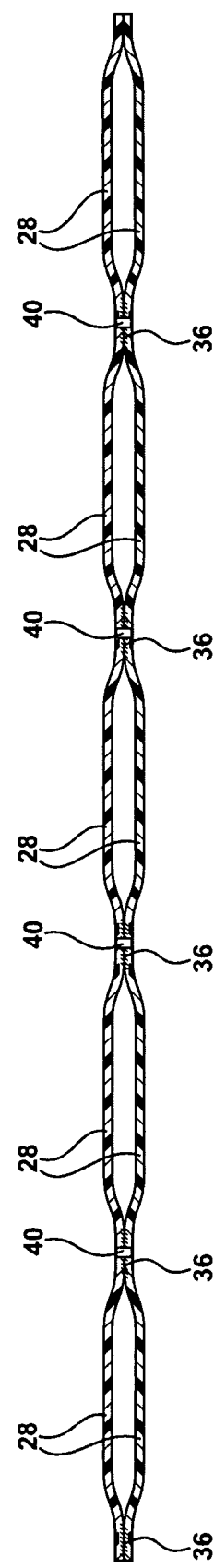

DISPOSABLE SHEATH FOR TELEMENTRY LEADS OF A MONITORING DEVICE

BACKGROUND OF THE INVENTION

1. Field of the Invention

A disposable sheath for covering telemetry leads extending from a monitoring device.

2. Description of the Prior Art

Telemetry leads, also known in the art as electrical leads, are used to connect monitoring devices to human patients for monitoring vital signs on humans. Normally, one end of each telemetry lead is coupled directly to a human for receiving the human's vital sign.

The telemetry lead is also in full contact with the human's skin along its length to the monitoring device and is exposed to germs and bacteria on the human body. An example is shown in U.S. Patent Application Publication No. 2002/0082644 (U.S. Pat. No. 6,662,056, issued Dec. 9, 2003), in the name of Picardo. Accordingly, the telemetry leads are disconnected from the human, cleaned and sterilized to kill germs before re-use on a patient. Proper cleaning and sterilization of the telemetry leads is necessary to eliminate the spread of secondary infections from one patient to another patient. Secondary infections can be spread from one patient to another because the telemetry leads are used repeatedly with various patients wherein the leads are in full contact with the patient's body. Because the telemetry leads are in direct contact with the human skin germs are easily transportable via the leads from one patient to another which can lead to a secondary infection in a subsequent patient.

SUMMARY OF THE INVENTION AND ADVANTAGES

In order to reduce the transmission of germs and bacteria between patients, the present invention is a disposable sheath for covering the electrical leads in a monitoring system used for monitoring patient vital signs. The sheath includes a pair of sheets having edges and a first end and a second end. The sheath is secured together along the edges and along spaced seams to define a plurality of longitudinally extending compartments. A plurality of tear lines extend along the spaced seams from the second end for laterally separating the compartments into separate arms wherein at least one electrical lead may be inserted into each arm.

The present invention of a disposable sheath provides a solution for reducing the risk of a secondary infection being transmitted from one patient to another patient during the repetitious use of the telemetry leads.

BRIEF DESCRIPTION OF THE DRAWINGS

Other advantages of the present invention will be readily appreciated, as the same becomes better understood by reference to the following detailed description when considered in connection with the accompanying drawings wherein:

FIG. 3 is an enlarged cross sectional view taken along line 2-2 of FIG. 2; and

FIG. 4 is an enlarged cross sectional view taken along line 3-3 of FIG. 2.

DETAILED DESCRIPTION OF THE INVENTION

Figure 1:
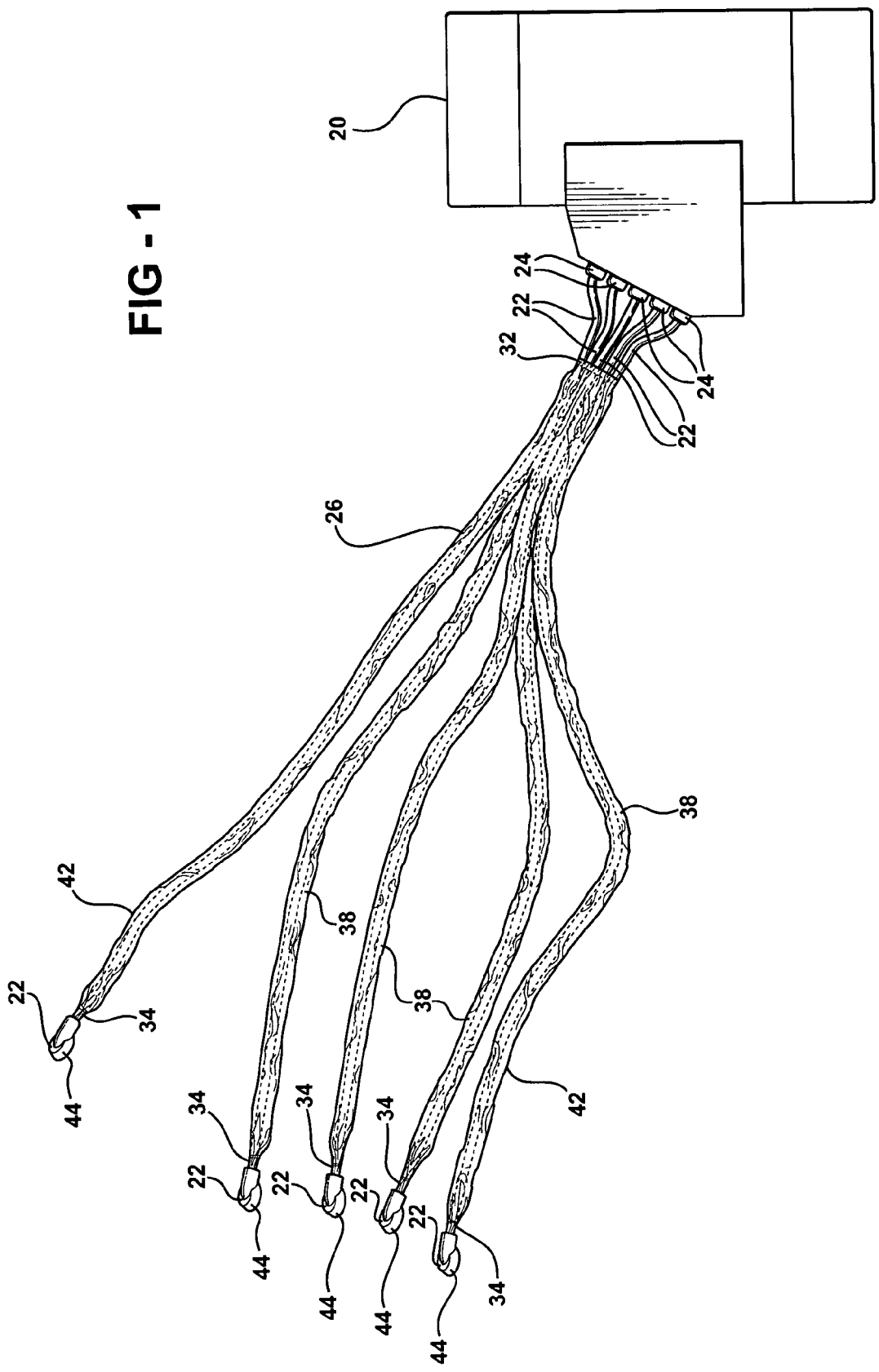
FIG. 1 is a perspective view of a monitoring device including a disposable sheath of the present invention.
Figure 2:
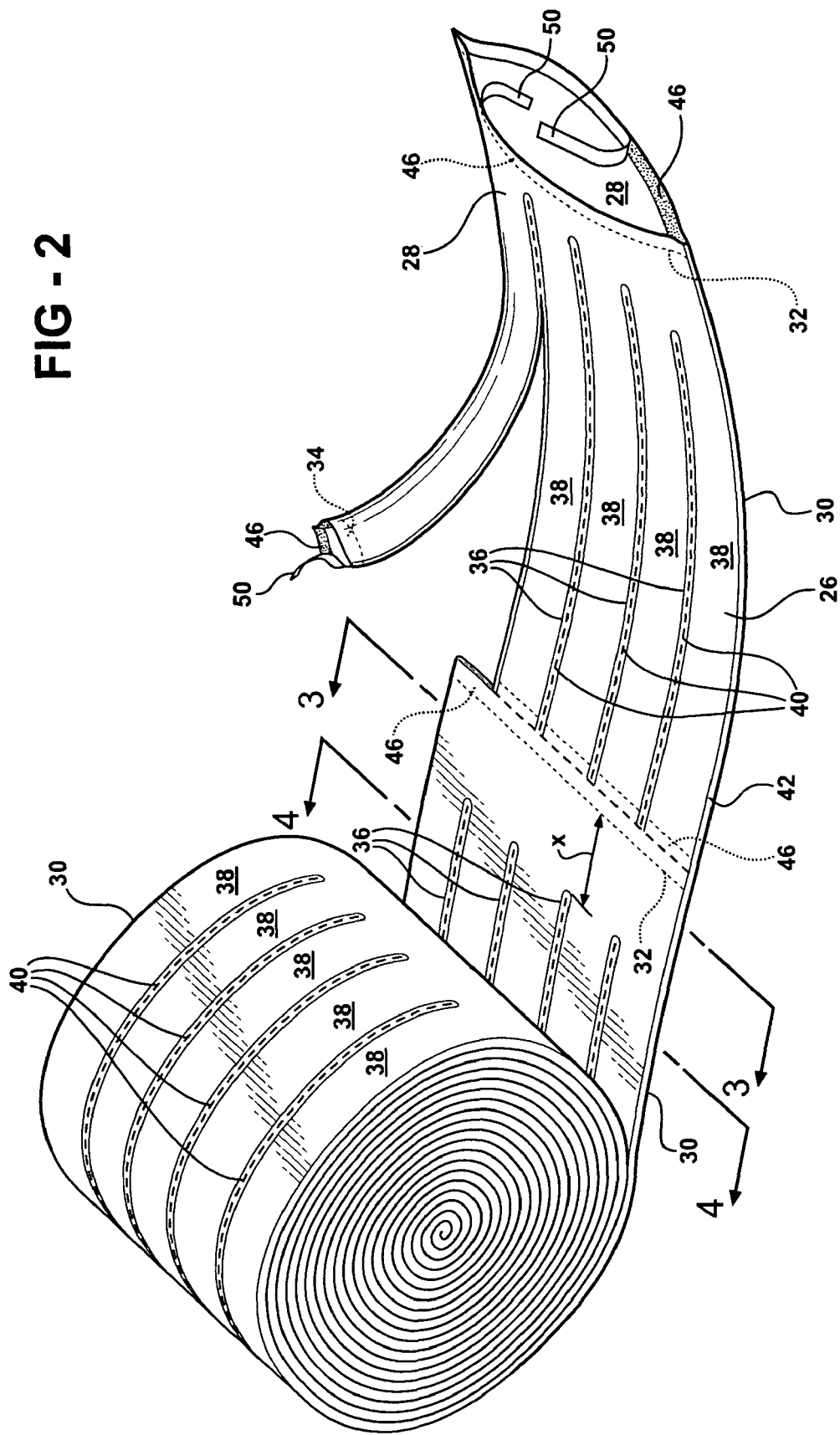
FIG. 2 is a top view of a plurality of disposable sheaths.

Referring to the Figures, a monitoring system for monitoring patient vital signs is shown in FIG. 1. The system includes a monitoring device 20 having a plurality of electrical leads 22 for engaging a human patient and monitoring the patient's vital signs. Each electrical lead 22 has an electrical conductive core (not shown) and a casing 24 that surrounds the core, as well known in the art.

The system further includes a sheath 26 generally indicated that is disposable. The sheath 26 includes a pair of sheets 28 having edges 30 and a first end 32 and a second end 34. The sheath 26 is secured together along the edges 30 and along spaced seams 36 and is distinguished by defining a plurality of longitudinally extending compartments 38. The sheets 28 may be bundled together by fusion in response to heat along the spaced seams 36. The electrical leads 22 of the monitoring device 20 extend into the compartments 38 at the first end 32 and out of the second end 34 of the sheath 26. As shown in the figures the electrical leads 22 are bundled together.

The sheath 26 may be fabricated from a variety of materials such as but not limited to latex or vinyl. For shipping purposes, a bundle of sheaths 26 may be disposed in an end to end relationship wherein each sheath 26 is separable from a plurality of sheaths 26.

The sheath 26 further includes a plurality of tear lines 40 that extend along the spaced seams 36 for laterally separating the compartments 38. The sheath 26 is separated along the tear lines 40 into separate arms 42 and at least one electrical lead 22 extends into each arm 42. As shown in the figures, the spaced seams 36 and tear lines 40 terminate at a distance X from the first end 32 and terminate at the second end 34 of the sheath 26. The tear lines 40 may be defined by a plurality of perforations extending through both sheets 28 along each seam 36.

At least one of the arms 42 of the sheath 26 includes a plurality of the compartments 38 which are separated into separate fingers 44 at the second end 34 of the sheath 36 along a tear line 40 extending between the compartments 38 of the arm 42. At least one electrical lead 22 extends from each finger 44.

The sheath 26 further includes a seal 46 disposed at each of the terminal ends 32, 34 for sealing the sheath 26 about the electrical leads 22 at the first terminal end 32 and about the electrical leads 22 extending from the second end 34. The seal 46 is adhesive and covered by a thin film of contact paper 50.

Obviously, many modifications and variations of the present invention are possible in light of the above teachings. The invention may be practiced otherwise than as specifically described within the scope of the appended claims.

What is claimed is:

1. A sheath for electrical leads in a monitoring system for monitoring patient physiological characteristics, said sheath comprising:

a pair of sheets having edges and a first end and a second end and being secured together along said edges and along spaced seams, the spaced seams beginning near the second end and running substantially parallel to said edges toward the first end to define a plurality of longitudinally extending compartments, the spaced seams ending a distance from the second end to define an open pocket between the edges at the second end, and a plurality of tear lines extending along said seams from said second end configured to laterally separate said compartments into separate arms, said pair of sheets being open at said first end configured to receive at least one electrical lead, each compartment being open at second end of said pair of sheets configured to allow a respective electrical lead to extend past said second end, each tear line being located between edges of a respective seam such that the seam remains sealed on adjacent arms when the tear line is separated.

2. A sheath as set forth in claim 1 wherein said seams terminate a distance from said first end and terminate at said second end for accommodating a plurality of electrical leads bundled together and extending into said sheath in said distance at said first end.

3. A sheath as set forth in claim 2 wherein at least one of the arms is separable into separate fingers at said second end for extending at least one electrical lead from each finger.

4. A sheath as set forth in claim 2 further including a seal disposed at each of said terminal ends for sealing said sheath about the electrical leads bundled together at said first terminal end and about the electrical leads extending from each of the arms.

5. A sheath, as set forth in claim 4, wherein the seal includes a layer of adhesive and a removable layer of paper.

6. An apparatus having a first sheath, the first sheath for electrical leads in a monitoring system for monitoring patient physiological characteristics, said sheath comprising:
   a pair of sheets having edges and a first end and a second end and being secured together along said edges and along at least one spaced seam to define a plurality of longitudinally extending compartments, the at least one spaced seams ending a distance from the first end to define an open pocket between the edges at the first end, and
   at least one tear line extending along said at least one spaced seam from said second end configured to laterally separate said compartments into separate arms, said pair of sheets being open at said first end configured to receive said electrical leads, each compartment being open at said second end of said pair of sheets configured to allow a respective electrical lead to extend past said second end, said at least one tear line being located between edges of a respective one of said at least one seam such that the seam remains sealed on adjacent arms when the tear line is separated.

7. An apparatus, as set forth in claim 6, further including a second sheath, the second sheath including:
   a pair of sheets having edges and a first end and a second end and being secured together along said edges and along at least one spaced seam to define a plurality of longitudinally extending compartments, and
   at least one tear line extending along said at least one spaced seam from said second end configured to laterally separate said compartments into separate arms for configured to extend at least one electrical lead into each arm, said at least one tear line being located between edges of a respective one of said at least one seam such that the seam remains sealed on adjacent arms when the tear line is separated, wherein the first end of the first sheath being removably attached to the second end of the second sheath.

8. An apparatus, as set forth in claim 7, wherein the first and second sheaths are provided on a roll.

9. An apparatus, as set forth in claim 6, further including a seal disposed at each of said terminal ends for sealing said sheath about the electrical leads bundled together at said first terminal end and about the electrical leads extending from each of the arms.

10. An apparatus, as set forth in claim 9, wherein the seal includes a layer of adhesive and a removable layer of paper.

* * * * *